United States Patent
Hwang et al.

(10) Patent No.: US 10,314,915 B2
(45) Date of Patent: Jun. 11, 2019

(54) CATECHIN BIOAVAILABILITY ENHANCER COMPRISING CYCLODEXTRIN

(71) Applicant: AMOREPACIFIC CORPORATION, Seoul (KR)

(72) Inventors: Jeong Ah Hwang, Yongin-si (KR); Yu Jin Oh, Yongin-si (KR); Young Kyung Kim, Yongin-si (KR); Jin Oh Chung, Yongin-si (KR); Sang Jun Lee, Yongin-si (KR); Soon Mi Shim, Yongin-si (KR); Jae Hwan Chung, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 6 days.

(21) Appl. No.: 14/437,626

(22) PCT Filed: Nov. 26, 2013

(86) PCT No.: PCT/KR2013/010792
§ 371 (c)(1),
(2) Date: Apr. 22, 2015

(87) PCT Pub. No.: WO2014/084572
PCT Pub. Date: Jun. 5, 2014

(65) Prior Publication Data
US 2015/0283251 A1 Oct. 8, 2015

(30) Foreign Application Priority Data
Nov. 30, 2012 (KR) .................. 10-2012-0137775

(51) Int. Cl.
| | |
|---|---|
| *A61K 31/047* | (2006.01) |
| *A61K 31/375* | (2006.01) |
| *A61K 9/00* | (2006.01) |
| *A61K 9/16* | (2006.01) |
| *A61K 9/20* | (2006.01) |
| *A23L 29/30* | (2016.01) |
| *A61K 31/00* | (2006.01) |
| *A61K 36/82* | (2006.01) |
| *A61K 47/40* | (2006.01) |
| *A61K 47/69* | (2017.01) |
| *A23L 33/105* | (2016.01) |
| *A61K 31/185* | (2006.01) |
| *A61K 31/194* | (2006.01) |
| *A61K 31/353* | (2006.01) |

(52) U.S. Cl.
CPC ............ *A61K 47/40* (2013.01); *A23L 29/35* (2016.08); *A23L 33/105* (2016.08); *A61K 9/009* (2013.01); *A61K 9/0095* (2013.01); *A61K 9/1652* (2013.01); *A61K 9/2059* (2013.01); *A61K 31/00* (2013.01); *A61K 31/047* (2013.01); *A61K 31/185* (2013.01); *A61K 31/194* (2013.01); *A61K 31/353* (2013.01); *A61K 31/375* (2013.01); *A61K 47/6951* (2017.08); *A61K 36/82* (2013.01)

(58) Field of Classification Search
CPC ................ A23L 1/3002; A61K 31/353; A61K 47/48969; A61K 36/82
See application file for complete search history.

(56) References Cited

U.S. PATENT DOCUMENTS

| | | | |
|---|---|---|---|
| 2006/0121158 A1 | 6/2006 | Ferruzzi et al. | |
| 2010/0179103 A1 | 7/2010 | Desai | |
| 2010/0209585 A1* | 8/2010 | Fukuda | A23F 3/30 426/591 |
| 2012/0083460 A1 | 4/2012 | Emura et al. | |
| 2012/0121761 A1* | 5/2012 | Fukuda | A23F 3/163 426/52 |

FOREIGN PATENT DOCUMENTS

| | | |
|---|---|---|
| CN | 1395922 | 2/2003 |
| JP | 2003286167 A | 10/2003 |
| JP | 2004238336 | 8/2004 |
| JP | 2006121973 A | 5/2006 |
| JP | 2006158379 | 6/2006 |
| JP | 2008079518 A | 4/2008 |
| JP | 2008301809 A | 12/2008 |
| JP | 2009184947 A | 8/2009 |

(Continued)

OTHER PUBLICATIONS

Munro et al., "Safety assessment of -cyclodextrin", Reg Toxicol Pharmacol 39: S3-S13 (2004).*
Terao et al., "Enhancement of oral bioavailability of coenzyme Q10 by complexation with γ-cyclodextrin in healthy adults", Nutrition Res 26: 503-508 (2006).*
Kuriyama, "The Relation between Green Tea Consumption and Cardiovascular Disease as Evidenced by Epidemiological Studies", J Nutr 138: 1548S-15533S (2008).*
Murase et al., "Reduction of diet-induced obesity by a combination of tea-catechin intake and regular swimming", International J Obesity 30: 561-568 (2006) (of record) (herein, Murase).*

(Continued)

*Primary Examiner* — John Pak
(74) *Attorney, Agent, or Firm* — Cantor Colburn LLP

(57) ABSTRACT

Disclosed is a catechin bioavailability enhancer comprising cyclodextrin as an active ingredient. Further, disclosed is a composition comprising a catechin bioavailability enhancer comprising catechin and cyclodextrin. The composition disclosed in the present specification may improve the stability of catechin which has significantly low intestinal absorption rate, and thus may improve bioaccessibility, intestinal transport rate and bioavailability of catechin. Accordingly, the improved bioavailability may further increase the effects of catechin such as the effects of reducing weight and body fat, anti-oxidative effects and anti-aging effects. The composition disclosed in the present specification having the above-mentioned characteristics can be effectively used in the fields of food or pharmacy.

4 Claims, 1 Drawing Sheet

(56) References Cited

FOREIGN PATENT DOCUMENTS

| | | | |
|---|---|---|---|
| JP | 2010168318 | 8/2010 | |
| JP | 5002072 B2 | 5/2012 | |
| JP | 2013123399 A | 6/2013 | |
| WO | 2009019876 A1 | 2/2009 | |
| WO | WO-2009019876 A1 * | 2/2009 | ............ A23F 3/163 |

OTHER PUBLICATIONS

Xu et al., "NMR studies on the interaction between (−)-epigallocatechin gallate and cyclodextrins, free and bonded to silica gels", Carbohydrate Res 342: 843-850 (2007).*
Li et al., "Chronic green tea catechins administration prevents oxidative stress-related brain aging in C57BL/6J mice", Brain Res 1353: 28-35 (2010).*
Surfactant—Synalloy Chemicals, 2016.*
Xu et al., Carbohydrate Res 342: 843 (2007) (Year: 2007).*
Terao et al., Nutrition Res 26: 503 (2006) (Year: 2006).*
Julian et al., Bioorganic & Medicinal Chem 15: 3217 (2007) (Year: 2007).*
Nakata et al., "Bioavailability enhancement of functional food materials by use of gamma cyclodextrin", Vitamins 84: 61-70 (2010) (Year: 2010)*
Murase et al., Int. J Obesity 30: 361 (2006) (Year: 2006).*
Hirsch, W. et al., "Connplexation of glucose by α- and β-cyclodextrins," Can. J. Chem., vol. 12, pp. 12-15 (1995).*
HCAPLUS abstract 2009:1416703; abstracting IT 1377728 (Jul. 26, 2010).*
International Search Report with English Translation for International Application No. PCT/KR2013/010792 dated Feb. 19, 2014.
Jullian, et al., ScienceDirect, Studies of inclusion complexes of natural and modified cyclodextrin with (+)catechin by NMR and molecular modeling, Bioorganic & Medicinal Chemistry 15 (2007), pp. 3217-3224.
Murase, et al., Original Article, Reduction of diet-induced obesity by a combination of tea-catechin intake and regular swimming, International Journal of Obesity (2006) 30, pp. 561-568.
Written Opinion for International Application No. PCT/KR2013/010792 dated Feb. 19, 2014.
Chinese Office Action—Chinese Application No. 201380057179.8 dated Feb. 27, 2017.
Zhen-Yu Chen et al., "Stabilizing Effect of Ascorbic Acid on Green Tea Catechins", J. Agric. Food Chem, (1998), vol. 46, pp. 2512-2516.
Japanese Office Action—Japanes Application No. 2015-545355 dated Jul. 4, 2017.
Japanese Office Action with Brief English Translation for Application No. 2015-545355 dated Nov. 28, 2017.
Nakata, et al., "Bioavailability Enhancement of Functional Food Materials by use of Gamma Cyclodextrin", Vitamins, 2010, vol. 84, Issue 2, pp. 61-70.

* cited by examiner

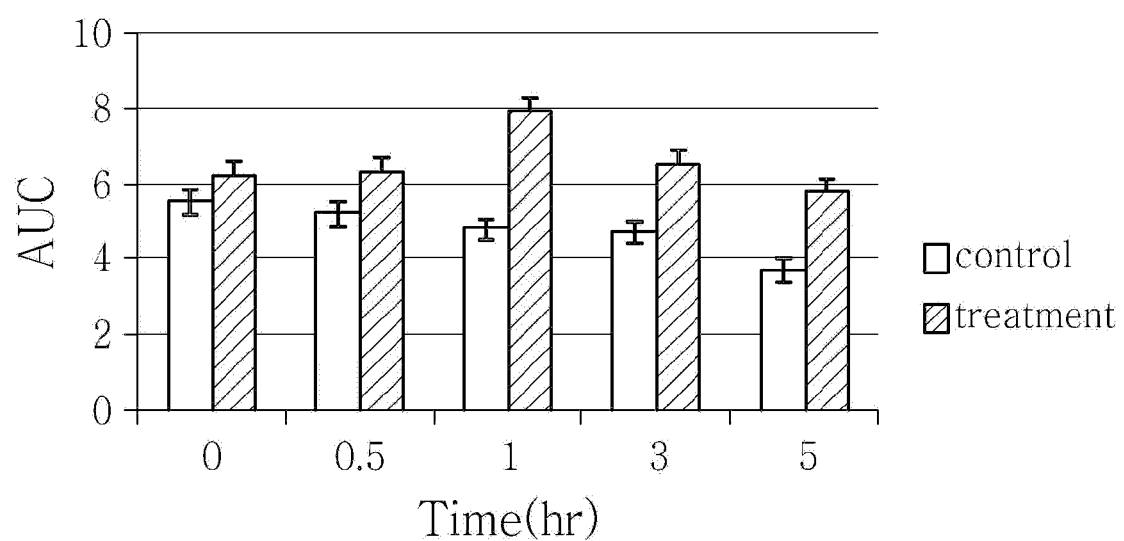

CATECHIN BIOAVAILABILITY ENHANCER COMPRISING CYCLODEXTRIN

TECHNICAL FIELD

The present invention relates to use of cyclodextrin for enhancing bioavailability of catechin.

BACKGROUND ART

Catechin, a kind of polyphenolic compound, is known to have various effects, such as an anti-viral effect, anti-cancer effect, effect of reducing cholesterol in blood, effect of reducing lipid in blood, effect of enhancing immunity and an anti-aging effect. Particularly, catechin is known to have excellent effect of reducing body fat and body weight. However, catechin has low stability under the condition of in vivo digestive fluid and a low absorption rate into small intestine cells and is subjected to rapid metabolism and secretion in digestive organs, and thus shows low bioavailability, resulting in low practical utility. Under these circumstances, many studies have been conducted to enhance bioavailability of catechin and practical utility thereof.

DISCLOSURE

Technical Problem

A technical problem to be solved by the present invention is to provide a formulation capable of enhancing bioavailability of catechin. Another technical problem to be solved by the present invention is to provide a composition having enhanced bioavailability of catechin.

Technical Solution

In one general aspect, there is provided a catechin bioavailability enhancer including cyclodextrin as an active ingredient.

In another general aspect, there is provided a composition including: catechin; and a catechin bioavailability enhance including cyclodextrin as an active ingredient.

In still another general aspect, there is provided a composition for reducing body weight and body fat, for anti-oxidation or for anti-aging, including catechin; and a catechin bioavailability enhancer including cyclodextrin as an active ingredient.

Advantageous Effects

According to the embodiments of the present invention, there is provided a catechin bioavailability enhancer including cyclodextrin as an active ingredient.

In addition, there is provided a composition including: catechin; and a catechin bioavailability enhancer including cyclodextrin as an active ingredient.

Further, there is provided a composition for reducing body weight and body fat, for anti-oxidation or for anti-aging, including catechin; and a catechin bioavailability enhancer including cyclodextrin as an active ingredient.

DESCRIPTION OF DRAWINGS

FIG. 1 is a graph illustrating the anti-oxidative activity of a composition containing catechin included in cyclodextrin, an acid and a sugar alcohol, as compared to that of a conventional catechin composition.

BEST MODE

In general, it is known that catechin is absorbed in intestines approximately at a level of less than 2% of the intake thereof. The reason why catechin has such low bioavailability is that catechin is sensitive to in vivo digestive fluid, and thus shows low stability and solubility in digestive organs. Another reason is that catechin shows a low absorption rate into small intestine cells and the metabolism and secretion of catechin are made rapidly in the small intestine.

In one aspect, there is provided a catechin bioavailability enhancer including cyclodextrin as an active ingredient. According to an embodiment, catechin is included in cyclodextrin so that the stability of catechin in digestive organs is enhanced. As a result, it is possible to enhance the bioaccessibility, intestinal transportability and bioavailability of catechin. In addition, when catechin bioavailability is enhanced by the inclusion of catechin in cyclodextrin, it is possible to realize the effects of catechin, including an effect of reducing body weight and body fat, anti-oxidation effect and an anti-aging effect, more sufficiently.

As used herein, 'catechin' includes effective ingredients contained in at least one extract of roots, stems, fruits, leaves, flowers and the other parts of a tea tree, i.e. *Camellia sinensis*. According to an embodiment, catechin includes (+)-catechin (C), (−)-epicatechin (EC), (−)-gallocatechin (GC), (−)-epigallocatechin (EGC), (−)-catechin gallate (CG), (−)-epicatechin gallate (ECG), (−)-gallocatechin gallate (GCG) and (−)-epigallocatechin gallate (EGCG). As used herein, 'extract' of *Camellia sinensis* is intended to cover a liquid of at least one extract of roots, stems, leaves, fruits, flowers and the other parts of *Camellia sinensis* before or after processing the same, a liquid obtained by steaming at least one of the above-mentioned parts and adding water thereto to carry out extraction, a liquid obtained by concentrating a liquid of at least one extract of the above-mentioned parts, and a solid formulation obtained by processing a liquid of at least one extract of the above-mentioned parts.

According to an embodiment, catechin may be included in the composition in the form of extract of *Camellia sinensis*, particularly tea extract. According to another embodiment, the tea extract may include catechin in an amount of at least 30 wt %, particularly at least 50 wt % based on the total weight of extract.

According to an embodiment, cyclodextrin includes one accepted as a food additive. In general, cyclodextrin as a food additive is used to increase the adhesive property and viscosity of food, to enhance emulsion stability and to improve the physical properties and feel of food. According to another embodiment, cyclodextrin includes at least one selected from the group consisting of alpha (α)-cyclodextrin, beta (β)-cyclodextrin and gamma (γ)-cyclodextrin.

In another aspect, there is provided a composition including: catechin; and a catechin bioavailability enhancer including cyclodextrin as an active ingredient. According to an embodiment, the composition may contain catechin included in cyclodextrin. According to another embodiment, the composition may contain catechin coated with cyclodextrin. The composition includes catechin in combination with cyclodextrin so that it has high bioaccessibility, intestinal transportability and bioavailability of catechin. In this manner, catechin realizes its effect more sufficiently and shows high utility. Particularly, the composition containing catechin and a catechin bioavailability enhancer including cyclodextrin has an excellent effect of reducing body weight and body fat, anti-oxidative effect and an anti-aging effect, such as an anti-skin aging effect.

According to an embodiment, the weight ratio of catechin to cyclodextrin may be 1,000:1 to 1:1,000, particularly 100:1 to 1:100, more particularly 1:10 to 10:1, and even more particularly 1:5 to 5:1. When the weight ratio is within the above-defined range, it is possible to realize the effects to be provided by the present invention adequately, to satisfy both the stability and safety of a composition, and to provide a cost-efficient effect.

According to an embodiment, the composition may further include at least one of an acid and sugar alcohol. When the composition further includes at least one of an acid and sugar alcohol, the bioaccessibility, intestinal transportability and bioavailability of catechin are further enhanced, and the accumulation rate of catechin in small intestine cells is increased, thereby providing the effects of catechin, such as an effect of reducing body weight and body fat, anti-oxidative effect and an anti-aging effect, more sufficiently.

As used herein, 'acid' means a material that is ionized upon dissolution in water to produce proton, and includes one accepted as a food additive. The acid as a food additive means one having a sour taste and used to increase acidity. According to an embodiment, the acid includes a weak acid, particularly an edible acid, such as an acid derived from natural food, such as fruits. More particularly, the acid may include at least one selected from the group consisting of citric acid, malic acid, tartaric acid, acetic acid, oxalic acid, tannin acid, butyric acid, lactic acid, glacial acetic acid and ascorbic acid.

As used herein, 'sugar alcohol' means an alcohol having at least two hydroxyl groups obtained by reduction of carbonyl groups of monosaccharide, or a compound that belongs to the same class, and includes one accepted as a food additive. According to an embodiment, sugar alcohol includes at least one sugarless sugar alcohol selected from the group consisting of xylitol, isomalt, maltitol, sorbitol, erythritol, mannitol, lactitol and Manatol. Such acid and sugar alcohol are low-calorie foods, and thus have no adverse influence on the effects for reducing body weight and body fat provided by the composition according to the present invention.

According to an embodiment, at least one of such an acid and sugar alcohol may be used each in an amount of 10-10,000 parts by weight, particularly 20-100 parts by weight or 100-1,000 parts by weight, based on 100 parts by weight of catechin. When the acid and sugar alcohol are used within the above-defined range, it is possible to realize the effects to be provided by the present invention adequately, to satisfy both the stability and safety of a composition, and to provide a cost-efficient effect. Particularly, it is preferred to use a sufficient amount of at least one of acid and sugar alcohol in order to enhance catechin bioavailability. Thus, at least one of an acid and sugar alcohol is used in an amount of at least 10 parts by weight based on 100 parts by weight of catechin. In addition, considering the total content applicable to the body, a content of 10,000 or higher is not acceptable.

According to an embodiment, the weight ratio of acid to sugar alcohol is 1,000:1 to 1:1,000, particularly 100:1 to 1:100, more particularly 1:10 to 10:1, and even more particularly 1:5 to 5:1. When the acid and sugar alcohol are used within the above-defined weight ratio, it is possible to realize the effects to be provided by the present invention adequately, to satisfy both the stability and safety of a composition, and to provide a cost-efficient effect.

In still another aspect, there is provided a food composition, including catechin; a catechin bioavailability enhancer including cyclodextrin; and optionally, at least one of an acid and sugar alcohol. According to an embodiment, the food composition may be health-aid food, functional food or a food additive composition. The composition may be applied to various formulations, including tablets, pellets, capsules, granule, liquid formulations such as drink, dietary bars and tea bags, through a conventional process including a step of adding various types of excipients or additives. The composition may further include the currently used ingredients other than the active ingredient, depending on the particular formulation and purpose, based on the selection of those skilled in the art. Combination with other ingredients may provide a synergic effect.

The effective dosage of active ingredient is determined by those skilled in the art. For example, daily dosage of catechin may be 100-1,000 mg, preferably 300-500 mg and may be administered at once or in three portions, but is not limited thereto. The daily dosage may be varied with various factors, such as the age, health condition or complications of a subject.

In yet another aspect, there is provided a pharmaceutical composition including: catechin; a catechin bioavailability enhancer including cyclodextrin and optionally, at least one of an acid and sugar alcohol. The pharmaceutical composition may have an effect of reducing body weight, effect of reducing body fat, and an effect of preventing and improving obesity. In addition, the pharmaceutical composition has excellent anti-oxidative activity and inhibits body aging, such as skin aging.

The pharmaceutical composition according to the present invention may further include a currently used inorganic or organic carrier added thereto, and may be administered orally in the form of a solid, semi-solid or liquid or administered via a rectal, local, transdermal, intravenous, intramuscular, intraperitoneal or subcutaneous route.

The formulations for oral administration may include tablets, pellets, soft and hard capsules, powder, granule, solution, emulsion, syrup or pellets. In addition, the formulations for parenteral administration may include injection formulations, drops, ointment, lotion, spray, suspension, oil and suppositories.

The pharmaceutical composition according to the present invention may be formulated with ease according to the conventional method, and a surfactant, excipient, colorant, fragrant, preservative, stabilizer, buffer, suspending agent or other conventional supplementary agents may be used as appropriate.

In addition, the dosage of active ingredient may be varied depending on the age, sex or body weight of a subject, condition of disease or pathology to be treated, administration route or judgment of a prescriber. Determination of dosage based on such factors is made by those skilled in the art. For example, 100-1,000 mg, preferably 300-500 mg of catechin may be administered once to three times per day. However, the scope of the present invention is not limited thereto.

Particular embodiments of the present invention are as follows.

1. A catechin bioavailability enhancer including cyclodextrin as an active ingredient, or a composition including: catechin; and a catechin bioavailability enhancer including cyclodextrin as an active ingredient, or a method for enhancing catechin bioavailability including a step of adding cyclodextrin to catechin or a composition including the same, or a method for enhancing catechin bioavailability including administering cyclodextrin in combination with catechin, or use of cyclodextrin for enhancing catechin bioavailability.

2. Item 1, wherein the cyclodextrin includes at least one selected from the group consisting of alpha-cyclodextrin, beta-cyclodextrin and gamma-cyclodextrin.

3. The composition including: catechin; and a catechin bioavailability enhancer as defined in Item 1 or 2.

4. Any one of Items 1 to 3, wherein the catechin is included in cyclodextrin.

5. Any one of Items 1 to 4, wherein the cyclodextrin is used in a weight ratio of 1:0.001 to 1:1,000 based on catechin.

6. Any one of Items 1 to 5 further including at least one of an acid and sugar alcohol.

7. Any one of Items 1 to 6 further including, as an acid, at least one selected from the group consisting of citric acid, malic acid, tartaric acid, acetic acid, oxalic acid, tannin acid, butyric acid, lactic acid, glacial acetic acid and ascorbic acid.

8. Any one of Items 1 to 7 further including, as a sugar alcohol, at least one selected from the group consisting of xylitol, isomalt, maltitol, sorbitol, erythritol, mannitol, lactitol and Manatol.

9. Any one of Items 1 to 8, wherein at least one of the acid and sugar alcohol is used in an amount of 10-10,000 parts by weight based on 100 parts by weight of catechin.

10. Any one of Items 1 to 9, wherein the composition is a composition for reducing body weight or body fat, the method is a method for reducing body weight or body fat, and the use is for reducing body weight or body fat.

11. Any one of Items 1 to 10, wherein the composition is a composition for anti-oxidation or anti-aging, the method is a method for anti-oxidation or anti-aging, and the use is for anti-oxidation or anti-aging.

The examples, comparative examples and test examples will now be described to illustrate the constitution and effects of the present invention in detail. The following examples, comparative examples and test examples are for illustrative purposes only and not intended to limit the scope of the present disclosure.

[Examples and Comparative Examples] Preparation of Catechin Composition

Tea leaves are extracted by using water and ethanol, and purified by a column to obtain tea extract having a catechin content of at least 50%. Then, the tea extract is used to provide a catechin-containing composition.

As cyclodextrin, used are commercially available alpha-, beta- and gamma-cyclodextrins, which are obtained by the action of transferase producing *Bacillus mecerans* and are used as food additives.

As ascorbic acid, used is a commercially available synthetic ascorbic acid, which is obtained by reacting glucose or sorbitol with alcohol to carry out esterification, followed by alkali treatment, and is used as a food additive.

As erythritol, used is a commercially available erythritol, which is obtained by filtering, purification, crystallization, washing with water and drying of fermented solution of *Moniliella pollinis* or *Trichosporonoides megachilensis* and is used as a food additive.

As xylitol, used is a commercially available xylitol, which is obtained by hydrogenation of xylose present in corns or birch trees as a basic material, and is used as a food additive.

The above ingredients are used to obtain each of Examples and Comparative Examples according to the formulations as shown in the following Table 1.

TABLE 1

| | Ingredients |
|---|---|
| Ex. 1 | Catechin 100 mg + Alpha-cyclodextrin 500 mg |
| Ex. 2 | Catechin 100 mg + Beta-cyclodextrin 500 mg |
| Ex. 3 | Catechin 100 mg + Gamma-cyclodextrin 500 mg |
| Ex. 4 | Catechin 100 mg + Gamma-cyclodextrin 500 mg + Ascorbic acid 30 mg |
| Ex. 5 | Catechin 100 mg + Gamma-cyclodextrin 500 mg + Ascorbic acid 30 mg + Erythritol 1000 mg |
| Ex. 6 | Catechin 100 mg + Gamma-cyclodextrin 500 mg + Ascorbic acid 30 mg + Xylitol 1000 mg |
| Comp. Ex. 1 | Catechin 100 mg |
| Comp. Ex. 2 | Catechin 100 mg + Ascorbic acid 30 mg |
| Comp. Ex. 3 | Catechin 100 mg + Ascorbic acid 30 mg + Erythritol 1000 mg |
| Comp. Ex. 4 | Catechin 100 mg + Ascorbic acid 30 mg + Xylitol 1000 mg |

[Test Example 1] Evaluation for Effect of Cyclodextrin Type on Catechin Bioavailability Absorption of catechin is determined when catechin is included in each of alpha ($\alpha$)-, beta ($\beta$)- and gamma ($\gamma$)-cyclodextrin to evaluate the catechin bioavailability of catechin.

Each of Examples 1 to 3 and Comparative Example 1 is cultured continuously in an artificial digestive solution that is an in vitro biomimic system in which the physiological and biochemical conditions of human digestive organs, i.e., mouth, stomach and small intestine, are simulated. The procedure will be described in detail hereinafter. First, 100 mg of each of Examples and Comparative Example is dissolved into phosphate buffer and amylase is added thereto, followed by nitrogen treatment, and each sample is cultured at 37° C. Then, pepsin solution is further added, pH is adjusted to 2 by using hydrochloric acid, and each sample is further cultured for 30 minutes. After that, sodium hydrogen carbonate ($NaHCO_3$) is added to adjust pH to 5.3. Then, a small intestine enzyme mixture is added and pH is adjusted to 7 by using NaOH solution. Treatment with nitrogen gas is carried out and each sample is cultured for 1 hour, followed by centrifugal separation. Then, a predetermined amount of sample is taken and the content of 4 types of epi-catechins (μg catechin/mg protein) is analyzed by ultra-high performance liquid chromatography (UPLC) to calculate bioaccessibility (%).

In addition, Caco-2 cells are used to obtain intestinal transportability (%). The procedure is as follows. Caco-2 cells are cultured in a trans-well medium and environment similar to the human small intestine is formed therein. Then, each of Examples and Comparative Example is introduced to the medium, cultured at 37° C. under 5% $CO_2$ for 1 hour, and analyzed by UPLC/MS/MSn. The results are shown in the following Table 2.

TABLE 2

| | Bioaccessibility (%) | Intestinal transportability (%) | Bioavailability (%) |
|---|---|---|---|
| Ex. 1 | 15.75 | 16.22 | 2.1 |
| Ex. 2 | 18.37 | 17.39 | 2.4 |

TABLE 2-continued

|  | Bioaccessibility (%) | Intestinal transportability (%) | Bioavailability (%) |
|---|---|---|---|
| Ex. 3 | 37.63 | 23.37 | 8.8 |
| Comp. Ex. 1 | 12.33 | 15.36 | 1.9 |

As can be seen from the above results, catechin included in alpha-, beta- or gamma-cyclodextrin shows higher bioaccessibility, intestinal transportability and bioavailability as compared to Comparative Example 1 including catechin alone. Particularly, catechin bioavailability of Example 3 (catechin included in gamma-cyclodextrin) is significantly higher as compared to Examples 1 and 2 (catechin included in alpha- and beta-cyclodextrin, respectively). This demonstrates that inclusion of catechin in cyclodextrin provides higher catechin bioaccessibility, intestinal accessibility and bioavailability as compared to catechin alone. Particularly, it can be seen that gamma-cyclodextrin provides the highest catechin bioaccessibility, intestinal accessibility and bioavailability among different types of cyclodextrins. Based on this, the following test is carried out by using catechin included in gamma-cyclodextrin.

[Test Example 2] Evaluation for Effect of Acid or Sugar Alcohol on Catechin Bioavailability A composition obtained by adding an acid or sugar alcohol to a composition containing catechin included in gamma-cyclodextrin is used to evaluate catechin bioaccessibility (%), intestinal accessibility (%) and bioavailability (%).

Examples 3 to 6 and Comparative Examples 1 and 2 are evaluated for catechin bioaccessibility, intestinal accessibility and bioavailability in the same manner as described in Test Example 1. The results are shown in the following Table 3.

TABLE 3

|  | Bioaccessibility (%) | Intestinal transportability (%) | Bioavailability (%) |
|---|---|---|---|
| Ex. 3 | 37.63 | 23.37 | 8.8 |
| Ex. 4 | 42.43 | 26.34 | 12.3 |
| Ex. 5 | 52.32 | 32.35 | 17.9 |
| Ex. 6 | 51.39 | 31.92 | 16.8 |
| Comp. Ex. 1 | 12.33 | 15.36 | 1.9 |
| Comp. Ex. 2 | 29.88 | 19.89 | 6.2 |

As can be seen from the above results, addition of ascorbic acid (Example 4), addition of ascorbic acid and a kind of sugar alcohol, erythritol (Example 5), or addition of ascorbic acid and a kind of sugar alcohol, xylitol (Example 6) to a composition of catechin included in cyclodextrin provides higher catechin bioaccessibility, intestinal accessibility and bioavailability. Particularly, when ascorbic acid is added as an acid and erythritol or xylitol is added as a sugar alcohol, catechin bioavailability is increased to about 10 times of the catechin bioavailability of Comparative Example 1. This suggests that an acid and sugar alcohol increase catechin bioavailability.

[Test Example 3] Evaluation for Bioavailability of Catechin Included in Cyclodextrin (Animal Test)

Fifty male ICR rats having an average body weight of 22.35 g are provided as test animals. The ICR rats are divided into five groups of 10 rats and classified into the control and Test groups 1 to 7. The test animals are raised preliminarily by using general compounded feed, and caused to start a fast 12 hours before the evaluation. Then, catechin included in cyclodextrin is administered orally to each test group as shown in Table 4.

TABLE 4

| | Test Procedure |
|---|---|
| Control | 100 mg of tea extract having a catechin content of 50% is administered orally to each test animal in a dose of 10 ml/kg |
| Test Group 1 | Composition obtained by mixing 100 mg of green tea extract having a catechin content of 50% with 30 mg of ascorbic acid in purified water is administered orally to each test animal in a dose of 10 ml/kg |
| Test Group 2 | Composition obtained by mixing 100 mg of green tea extract having a catechin content of 50% with 30 mg of ascorbic acid and 1000 mg of erythritol in purified water is administered orally to each test animal in a dose of 10 ml/kg |
| Test Group 3 | Composition obtained by mixing 100 mg of green tea extract having a catechin content of 50% with 30 mg of ascorbic acid and 1000 mg of xylitol in purified water is administered orally to each test animal in a dose of 10 ml/kg |
| Test Group 4 | 100 mg of green tea extract containing 50% of catechin included in gamma-cyclodextrin is administered orally to each test animal in a dose of 10 ml/kg |
| Test Group 5 | Composition obtained by mixing 100 mg of green tea extract containing 50% of catechin included in gamma-cyclodextrin with 30 mg of ascorbic acid in purified water is administered orally to each test animal in a dose of 10 ml/kg |
| Test Group 6 | Composition obtained by mixing 100 mg of green tea extract containing 50% of catechin included in gamma-cyclodextrin with 30 mg of ascorbic acid and 1000 mg of erythritol in purified water is administered orally to each test animal in a dose of 10 ml/kg |
| Test Group 7 | Composition obtained by mixing 100 mg of green tea extract containing 50% of catechin included in gamma-cyclodextrin with 30 mg of ascorbic acid and 1000 mg of xylitol in purified water is administered orally to each test animal in a dose of 10 ml/kg |

Then, 8 weeks after the oral administration, the animals in each test group are weighed. The results are shown in the following Table 5.

TABLE 5

| Group | Control | Test Group | | |
|---|---|---|---|---|
| Decrease in Body weight ($\Delta$g) | 0.2 ± 0.65 | Test Group 1 | Test Group 2 | Test Group 3 |
| | | 1.4 ± 0.39 | 2.1 ± 0.31 | 3.2 ± 0.24 |
| | | Test Group 4 | Test Group 5 | Test Group 6 | Test Group 7 |
| | | 0.9 ± 0.27 | 1.6 ± 0.13 | 3.6 ± 0.49 | 3.4 ± 0.88 |

As can be seen from the above results, catechin included in gamma-cyclodextrin provides a higher effect of reducing body weight as compared to catechin alone, and the effect is the highest when a composition containing catechin included in cyclodextrin, ascorbic acid and erythritol or xylitol is administered. In addition, catechin included in cyclodextrin provides a higher effect of reducing body weight as compared to a composition containing catechin non-included in cyclodextrin, ascorbic acid and a sugar alcohol. This suggests that an excellent effect of enhancing catechin bioavailability is provided by gamma-cyclodextrin, and inclusion of catechin in cyclodextrin in combination with addition of an acid and sugar alcohol provides even higher catechin bioavailability.

In other words, a composition containing catechin included in cyclodextrin, an acid and sugar alcohol has an excellent effect of reducing body weight.

[Test Example 4] Evaluation for Bioavailability of Catechin Included in Cyclodextrin (Clinical Test)

A composition containing catechin included in cyclodextrin and another composition containing the same composition together with an acid and sugar alcohol are evaluated for their effects of reducing body weight and body fat through a clinical test. As test subjects, 20-60 aged adults suffering from overweight or abdominal obesity and having a percent of ideal body weight (% IBW) of 110% or more or a waist length of at least 90 cm (male) or 80 cm (female) and a body mass index (BMI) of 25 more are selected. The characteristics of subjects in each test group are shown in the following Table 6.

TABLE 6

|  | Test Group (n = 30) | Control (n = 15) |
|---|---|---|
| Age | 35.2 ± 7.3 | 35.7 ± 2.5 |
| Height (m) | 166.1 ± 2.5 | 165.9 ± 9.2 |

Particularly, 45 subjects are divided into three groups, each having 15 subjects (7 males and 8 females). One group (Test Group 1) is allowed to take the composition of Example 5, another group (Test Group 2) is allowed to take the composition of Comparative Example 3, and the other group (Control) is allowed to take the composition of Comparative Example 1, after meal, three times per day, every day for 12 weeks. After 12 weeks, the average physical indices of each group are shown in the following Table 7 as compared to those of each group before the test.

TABLE 7

|  | Test Group 1 (n = 15) | | Test Group 2 (n = 15) | | Control (n = 15) | |
|---|---|---|---|---|---|---|
|  | 0 week | 12 weeks | 0 week | 12 weeks | 0 week | 12 weeks |
| BMI(Kg/m$^2$) | 27.9 ± 0.58 | 26.0 ± 0.33 | 27.4 ± 0.43 | 26.5 ± 0.27 | 27.3 ± 0.42 | 27.2 ± 0.43 |
| Body fat (%) | 38.8 ± 1.25 | 36.1 ± 1.37 | 39.1 ± 1.21 | 37.1 ± 1.91 | 38.2 ± 1.13 | 38.1 ± 1.74 |
| Body weight decrease (Δkg) | — | 4.3 ± 0.59 | — | 4.0 ± 0.61 | — | 1.4 ± 0.27 |

As can be seen from the above results, in Test Groups 1, the body weight, BMI and body fat decrease at the same time, a statistical significance (p<0.05) is provided, and higher effects of reducing body weight, BMI and body fat are provided as compared to Test Group 2. On the contrary, in the control, all indices show little change. In other words, the above clinical test results demonstrate that the composition obtained by inclusion of catechin in cyclodextrin and incorporation of an acid and sugar alcohol allows catechin to provide maximized effects of reducing body weight and body fat.

[Test Example 5] Evaluation for Anti-Oxidative Effect of Catechin Included in Cyclodextrin (Clinical Test)

A composition containing catechin included in cyclodextrin, an acid and sugar alcohol is evaluated for its anti-oxidative effects through a clinical test. As test subjects, 20-30 aged healthy adults are selected. The characteristics of test subjects in each test group are shown in the following Table 8.

TABLE 8

|  | Test Group (n = 10) | Control (n = 10) |
|---|---|---|
| Age | 32.5 ± 4.5 | 32.0 ± 2.5 |
| Height (m) | 166.4 ± 6.0 | 165.9 ± 3.5 |
| Body weight (kg) | 53.5 ± 10.0 | 53.0 ± 8.5 |

The test group is allowed to take the composition of Example 6 and the control is allowed to take the composition of Comparative Example 1 in the form of tablets, 3 tablets per day, together with 100 mL of water. After the lapse of a predetermined time (before intake and 0.5, 1, 3 and 5 hours after the intake), blood samples are taken to evaluate the anti-oxidative activity in the plasma. The results are shown in FIG. 1.

As can be seen from FIG. 1, the test group provides higher anti-oxidative activity any times after the intake as compared to the control, and shows a statistical significance (p<0.05). In other words, the above clinical test results demonstrate that the composition obtained by inclusion of catechin in gamma-cyclodextrin and incorporation of an acid and sugar alcohol has a higher anti-oxidative effect as compared to a composition containing catechin alone. Further, since the composition containing catechin included in cyclodextrin, an acid and sugar alcohol has high anti-oxidative activity, it inhibits active oxygen that causes aging, so that it may have an excellent effect of improving aging conditions, such as a decrease in skin elasticity and an increase in skin wrinkles.

Some formulation examples of the composition according to an embodiment of the present invention will be explained hereinafter for illustrative purposes only. However, the present invention may be embodied in many different forms and should not be construed as limited to the exemplary embodiments set forth therein.

[Formulation Example 1] Preparation of Health-Aid Drink

| Example | 1000 mg |
|---|---|
| Enzyme-treated stevia | 100 mg |
| Apple juice concentrate | 2 g |
| Hibiscus extract | 100 mg |
| Taurin | 1 g |
| Add purified water to total | 1000 ml |

The above ingredients are mixed according to a conventional method for preparing a health-aid drink, and heated under agitation at 80-90° C. for about 1 hour. Then, the resultant solution is filtered, introduced into a sterilized container, sealed and sterilized, and then stored in a refrigerator so that it may be used to prepare a health-aid drink composition. In this Example, the ingredients suitable for a health-aid drink are mixed and formulated as necessary. However, the particular composition may be varied according to the local or national preference including people or country requiring the drink, particular use, etc.

[Formulation Example 2] Pellets

First, 20 wt % of tea extract having a catechin content of 50%, 10 wt % of gamma-cyclodextrin, 10 wt % of citric acid, 10 wt % of erythritol, 10 wt % of corn starch, 20 wt % of glycerin and 10 wt % of sorbitol are mixed. Then, the resultant mixture is pelletized by a pelletizing machine to obtain pellets.

[Formulation Example 3] Tablets

First, 30.5 wt % of tea extract having a catechin content of 50%, 10 wt % of gamma-cyclodextrin, 10 wt % of ascorbic acid, 7 wt % of erythritol and 20 wt % of crystalline cellulose are mixed. Then, the resultant mixture is granulated by using a fluidized bed dryer and 2.5 wt % of sugar ester is added thereto, followed by compression into tablets.

[Formulation Example 4] Granules

First, 20 wt % of tea extract having a catechin content of 30%, 10 wt % of gamma-cyclodextrin, 10 wt % of ascorbic acid, 10 wt % of erythritol, 5 wt % of enzyme-treated *stevia* and 45 wt % of isomalt are mixed. Then, the resultant mixture is formed into granules by using a fluidized-bed granulating machine, followed by packaging into sachets.

The invention claimed is:

1. A method for enhancing catechin bioavailability comprising administering an effective amount of a composition comprising catechin; acid; sugar alcohol; and gamma-cyclodextrin to a subject in need thereof,
    wherein the catechin is encapsulated into gamma-cyclodextrin,
    wherein the composition comprises the acid in an amount of 20-100 parts by weight and the sugar alcohol in an amount of 100-1,000 parts by weight, based on 100 parts by weight of the catechin, and
    wherein the method is for reducing body weight or body fat.

2. The method according to claim 1, wherein the gamma-cyclodextrin is comprised in a weight ratio of 1,000:1 to 1:1,000 based on catechin.

3. The method according to claim 1, wherein the acid comprises at least one selected from the group consisting of citric acid, malic acid, tartaric acid, acetic acid, oxalic acid, tannin acid, butyric acid, lactic acid, glacial acetic acid, and ascorbic acid.

4. The method according to claim 1, wherein the sugar alcohol comprises at least one selected from the group consisting of xylitol, isomalt, maltitol, sorbitol, erythritol, mannitol, and lactitol.

* * * * *